United States Patent [19]

Pickhard

[11] Patent Number: 5,226,881
[45] Date of Patent: Jul. 13, 1993

[54] INJECTION SYRINGE WITH A SAFEGUARD AGAINST REUSE

[76] Inventor: Ewald Pickhard, Redtenbachergasse 15, A-1160 Wien, Austria

[21] Appl. No.: 659,283
[22] PCT Filed: Oct. 13, 1989
[86] PCT No.: PCT/AT89/00090
   § 371 Date: May 24, 1991
   § 102(e) Date: May 24, 1991
[87] PCT Pub. No.: WO90/03817
   PCT Pub. Date: Apr. 19, 1990

[30] Foreign Application Priority Data

Oct. 13, 1988 [AT] Austria .................... 2549/88
May 11, 1989 [AT] Austria .................... 1131/89

[51] Int. Cl.[5] .................................. A61M 5/00
[52] U.S. Cl. ............................ 604/110; 604/218
[58] Field of Search ............ 604/110, 187, 218, 228, 604/222, 231, 203

[56] References Cited

U.S. PATENT DOCUMENTS 4,863,427  9/1989  Cocchi ........................... 604/110

FOREIGN PATENT DOCUMENTS 2207054  1/1989  United Kingdom ............ 604/110

Primary Examiner—John D. Yasko
Attorney, Agent, or Firm—Collard & Roe

[57] ABSTRACT

An injection device (1) has an injection cylinder (2), a piston (8) arranged in the injection cylinder (2) connected preferably by means of coupling means (7) to a piston rod (6) that is preferably longer than the injection cylinder (2). An injection needle (4) may be coupled to the injection cylinder (2) by coupling means (3) arranged on the side of the injection cylinder (2) opposite the piston rod (6). Means (201) that prevent the injection device from being re-used are provided with opening means (215) linked to the piston (8) and/or to the piston rod (6) and/or to the injection cylinder or arranged therebetween and are associated with the piston (8) and/or the piston rod (6).

7 Claims, 4 Drawing Sheets

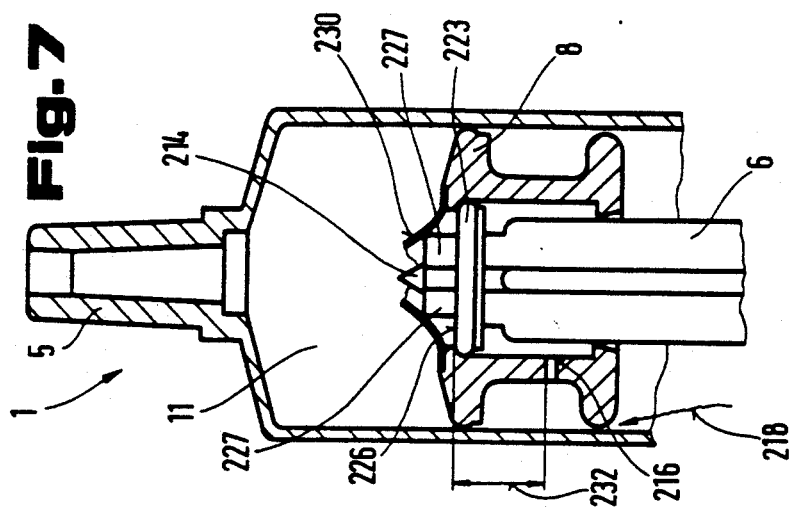
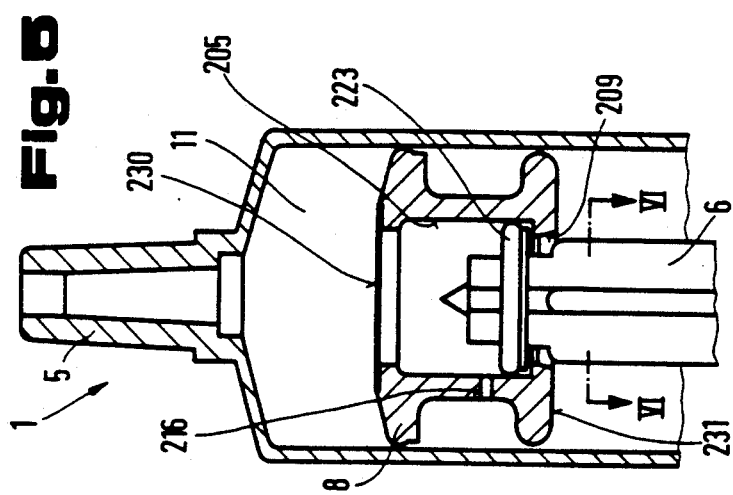
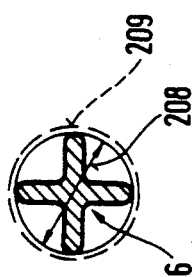
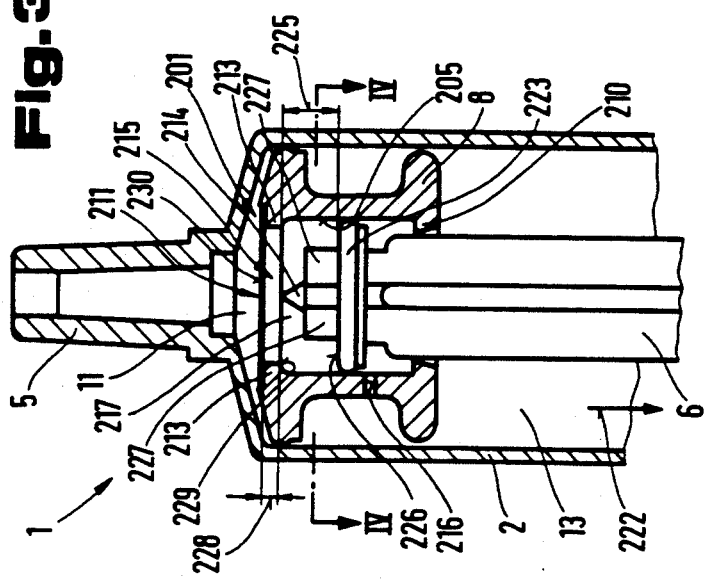
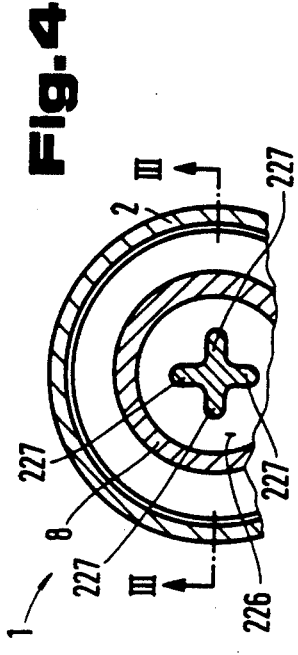

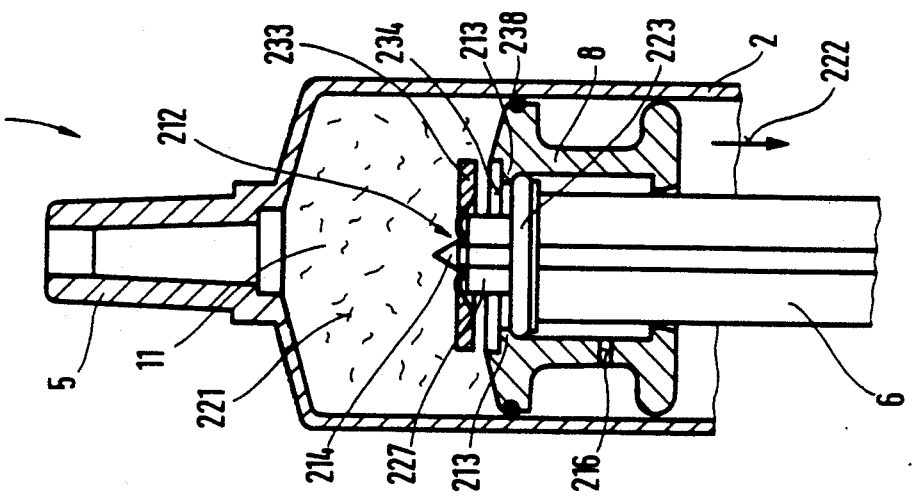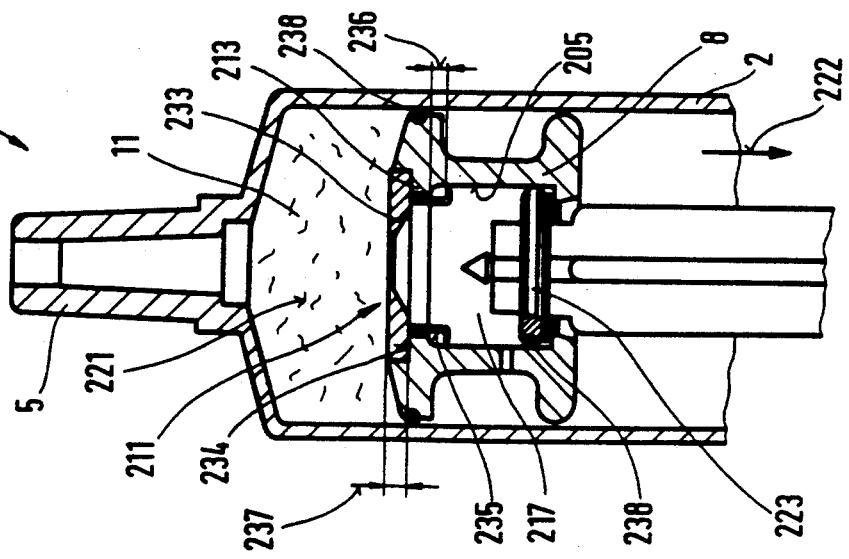

INJECTION SYRINGE WITH A SAFEGUARD AGAINST REUSE

BACKGROUND OF THE INVENTION

1. Field of the Invention

The present invention relates to an injection syringe comprising a cylinder having a longitudinal axis extending between opposite ends of the cylinder, a piston guided in the cylinder and dividing the cylinder into two cylinder chambers respectively facing the opposite cylinder ends, a piston rod preferably having a length exceeding that of the cylinder and coupled to the piston, the piston rod extending in one cylinder chamber and through one cylinder end, a coupling arrangement at a cylinder end opposite to the one end for coupling an injection needle held by the coupling arrangement to the cylinder, the piston and the opposite cylinder end defining the other cylinder chamber, and a safeguard against reuse of the injection syringe, the safeguard comprising an opening member between the piston and the piston rod.

2. Description of the Prior Art

A non-reusable syringe of this type is disclosed in British patent No. 2,207,054. The opening member is formed by a stopper connected to the piston rod, and when the injection fluid is pressed out by the piston, the stopper must be pushed through to connect the chamber containing the fluid to the ambient atmosphere so that no further suction is applied to the medicament. The end of the piston may also be equipped with a deformable sealing membrane which is pressed against an opening spike when pressure is applied to the piston to squeeze the injection fluid out. This is designed to damage the sealing membrane and prevent further fluid from being drawn up by the syringe. This structure has the disadvantage that even a slight operating error, for example while the injection fluid is drawn up, may damage the syringe and make it useless.

French patent No. 2,606,643 discloses a somewhat similar syringe and its safeguard against re-use at an end wall of the cylinder facing the needle comprises an opening member connected to the cylinder and pointing towards the piston. A sealing membrane in the vicinity of the piston is associated with the opening membrane. When the piston is moved forward by the piston rod into abutment with the end wall of the cylinder, the sealing membrane will be opened and no further injection fluid can be drawn up into the cylinder so that the syringe cannot be re-used. The disadvantage is that injection fluid could be drawn up in succession several times and administered to successive patients if the cylinder is not completely emptied, i.e. if the piston is not moved forward into abutment with the cylinder end wall. Therefore, re-use cannot be reliably prevented.

Other types of non-reusable syringes are also known. To avoid re-use, Published British Patent Application No. 2,195,537 proposes to surround the injection needle with a protective sheath. When this is removed for use of the syringe, one can see that the protective seal has been broken.

It is also known to provide seals formed by membranes between the needle and the cylinder of the syringe. These are only pierced immediately before the syringe is used so that the medicament is hermetically sealed in the cylinder until the syringe is actually used. The disadvantage of these syringes is that more medicament may be sucked into the cylinder when medicament has been discharged therefrom by operating the piston so that the syringe may be used a second time. In other words, such syringes are re-usable, which constitutes a danger particularly in countries with little awareness of hygiene, and may lead to an epidemic spread of contagious diseases, such as AIDS.

SUMMARY OF THE INVENTION

It is the primary object of this invention to provide an injection syringe which cannot take in more medicament even when only a small amount of medicament has been discharged.

The above object is accomplished according to the invention in an injection syringe of the first-indicated type with a safeguard against re-use which comprises an inner piston connected to the piston rod for movement therewith and guided in a bore in the piston, the bore extending parallel to the longitudinal cylinder axis, and respective stops delimiting the piston bore towards the other cylinder chamber and the piston rod whereby the inner piston is coupled to the piston, the stops projecting inwardly into the path of the movement of the inner piston in the bore for engagement with the inner piston. A frangible sealing element is arranged at an end of the bore remote from the piston rod for sealing the bore from the other cylinder chamber and a piercing spike projects from an end of the inner piston facing the sealing element for opening the frangible sealing element upon movement of the inner piston towards the remote bore end. A venting aperture in the piston is spaced from the remote bore end and connects the piston bore with the ambient atmosphere, the venting aperture being positioned between the inner piston and the sealing element when the inner piston engages the stop delimiting the piston bore towards the piston rod.

Such a syringe will be reliably safeguarded against re-use. The frangible sealing element is pierced by the spike of the inner piston when the piston is pushed forward when the injection fluid is first squeezed out of the other cylinder chamber. Hence, no multiple use is possible even if not all the fluid has been discharged. With the double-piston arrangement, a small amount of fluid can still be sucked up with the inner piston inside the main piston even when the sealing element has been pierced, as is necessary, for example, for so-called aspiration. However, a larger amount of injection fluid cannot be drawn up into the other cylinder chamber by operation of the main piston. The other cylinder chamber will necessarily be connected to the ambient atmosphere by operation of the piercing spike on the inner piston when the same is withdrawn to draw up more fluid. Consequently, it will be impossible to create a partial vacuum in the other cylinder chamber to draw in more fluid. Therefore, the syringe is made useless.

Preferably, the piston rod, the piston, the inner piston, the piercing spike and the sealing element are arranged coaxially along the longitudinal cylinder axis. This assures a correct operation of the piercing spike when strong compressive forces are applied thereto to pierce the sealing element.

A reliable way of preventing undesirable air bubbles between the sealing element and the inner piston is assured by providing spreading elements projecting from the end of the inner piston and arranged radially adjacent the piercing spike. If the spreading elements are lifted off the spike, the fluid can reliably flow between the sealing element and the inner surface of the piston and squeeze out the air.

If piston rings are arranged respectively between the piston and the cylinder, and the inner piston and the piston bore, a better seal is obtained so that a higher discharge pressure can be built up. Furthermore, when the injection fluid is discharged during the first use, it can be prevented from passing undesirably towards the piston rod, with a consequent loss of fluid.

According to another preferred feature, retaining members mount the sealing element in an opening in the opposite cylinder end and engage the stop delimiting the piston bore towards the other cylinder chamber, and a distance between the sealing element and the stop is greater than the depth of the opening. This ensures that the sealing element cannot enter the other cylinder chamber when it is pierced, thereby preventing the fluid from passing out through the injection needle.

Also, the piercing spike preferably has a length extending from the end of the inner piston which is greater than the distance between the sealing element and abutment faces of the stops engaged by the inner piston. This ensures that the sealing element will definitely be punctured, even allowing for the tolerances which can never be entirely avoided in industrial production, and guarantees reliable operation of the syringe.

BRIEF DESCRIPTION OF THE DRAWING

The above and other objects, advantages and features of the present invention will now be described in the following detailed description of certain now preferred embodiments, taken in conjunction with the accompanying drawing wherein

FIG. 3 is a fragmentary side view of a different embodiment of a syringe according to the invention, in a section taken along lines III—III in FIG. 4;

FIG. 4 is a fragmentary end view of the syringe in a cross section taken along lines IV—IV in FIG. 3;

FIG. 5 shows the syringe of FIG. 3, while injection fluid is being drawn up into its interior;

FIG. 6 is an end view of the piston rod of the syringe of FIGS. 3 to 5, in a cross section taken along lines VI-VI in FIG. 5;

FIG. 7 shows the syringe of FIGS. 3 to 6 in a position where the injection fluid is being pressed out of its interior with the sealing element broken;

FIG. 8 is a cross sectional side view of a different embodiment of a syringe according to the invention, in the position where an injection fluid is being drawn up into the interior;

FIG. 9 shows the syringe of FIG. 8 in the position where the injection fluid is being sucked or pressed out of the interior;

FIG. 10 shows the syringe of FIGS. 8 and 9 during the suction process, with the piston rod drawn back;

DETAILED DESCRIPTION OF PREFERRED EMBODIMENTS

Figure 1:
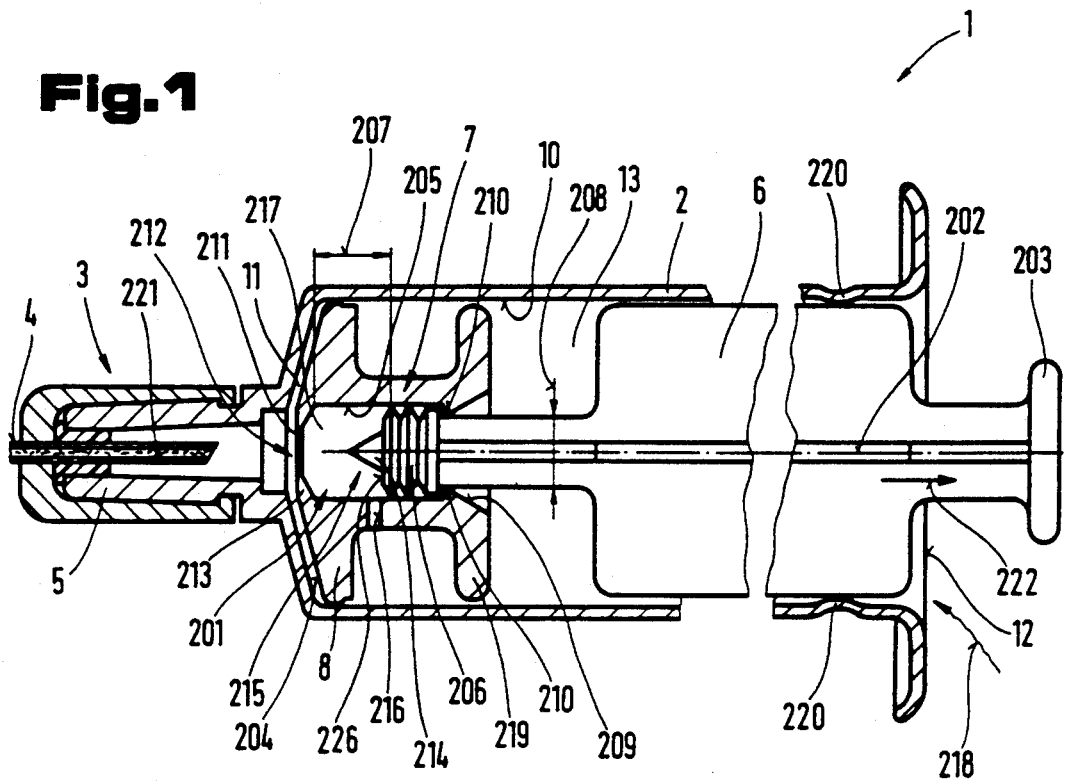
FIG. 1 is a side elevation, partly in cross section, of an injection syringe according to the invention, in a greatly simplified diagrammatic representation.

FIG. 1 shows an injection syringe 1 comprising a cylinder 2 and an injection needle 4 connected thereto by a coupling arrangement 3. The coupling arrangement 3 is arranged on a tubular outlet 5 of the cylinder 2. A piston rod 6 is located inside the cylinder 2 and is displaceable longitudinally thereof. It is connected by a coupling device 7 to a piston 8 for movement therewith. A safeguard against reuse 201 is associated with the coupling device 7. The piston 8 may be a rubber or plastics member or a suitable plastics insert with sealing elements such as O-rings or rubber packings or the like arranged at its periphery. The rubber packings or O-rings of the piston lie against an inner wall 10 of the cylinder 2 and divide it into a cylindrical chamber 11 communicating with the outlet 5, and a cylindrical chamber 13 associated with an opening 12 of the cylinder 2.

The piston rod 6 is provided with a manipulating knob 203 which can operate it and displace it along a longitudinal axis 202 of the cylinder 2. Knob 203 projects from the cylinder 2 in a position where the end face 204 of the piston 8 is in contact with the end wall of the cylinder 2 facing towards the injection needle 4. The position illustrated also corresponds to the packed state of a syringe 1 according to the invention, although in that case the injection needle 4 would not yet be pushed onto the outlet 5.

The piston 8 has a bore 205 in which an inner piston 206 is mounted for displacement in the direction of the longitudinal axis 202. The inner piston 206 is connected for movement with the piston rod 6. Over a length corresponding to the length 207 of the stroke of the inner piston, the piston rod 6 has a diameter 208 substantially corresponding to that of an inlet 209 left open between stops 210 delimiting the bore 205. The diameter 208 is smaller than that of the cylindrical chamber 13 which extends between four piston rod fins spaced 90° from one another.

The end bore 205 opposite the inlet opening 209 is closed by a frangible sealing element 211 which has a weakened section 212. The sealing element may be formed by the end face 204 of the piston 8 or by a section with a thinner wall. Stops 213 may be provided on both sides of the weakened section 212, and may similarly be formed by thickening the wall in the end face 204 of the piston 8. The inner piston 206 is engaged by the stops 213 when it is pressed towards the piston 8 with the piston rod 6. The inner piston 206 further has a piercing spike 214 forming an opening member 215 for opening the sealing element and its weakened section 212.

A venting aperture 216 in the piston 8 connects an internal space 217 in the bore 205 with ambient atmosphere 218, which also is connected with the cylindrical chamber 13.

The piston 8 may further be provided with a projection 219 to guide it. The projection does not form a seal with the inner wall 10 of the cylinder 2 but it does prevent the piston 8 from assuming an inclined position to the longitudinal axis 202 when it is displaced.

As indicated diagrammatically, the cylinder 2 has projecting bumps or wart-like raised portions 220 projecting into the cylindrical chamber 13 in the region of its opening 12, and which may be distributed along the periphery of the cylinder. The injection fluid, e.g. a medicament or blood, is indicated at 221. The purpose of the raised portions 220 is to prevent the piston 8 from being withdrawn from the cylinder 2 unless sufficient force is applied to overcome a resistance when an injection fluid 221 is being drawn up in the needle 4. Thus, accidental withdrawal of the piston 8 is avoided. However, the raised portions 220 must not be too high and the elasticity of the piston rings on the piston 8 must be sufficient to enable the piston 8 to be inserted in the cylinder 2 from the opening 12.

In the FIG. 1 position, injection fluid is sucked into the cylindrical chamber 11 by pulling out the piston rod 6 in the direction of arrow 222, for which purpose piston 8 is moved towards the opening 12. An adequate partial vacuum is formed in the chamber 11 while the injection fluid 221 is being sucked in since the end face 204 of the piston 8 seals off the cylinder 2 from the opening 12.

If sufficient injection fluid is contained in the chamber 11, and if this is to be injected into an animal or human body, the piston rod 6 must be pressed by means of the knob 203 towards the injection needle 4 in the opposite direction to the arrow 222. The resistance set up by injection fluid 221 to movement of the piston 8 towards the needle 4 causes the inner piston 206 to be displaced first within the bore 205 relative to the piston 8.

Figure 2:
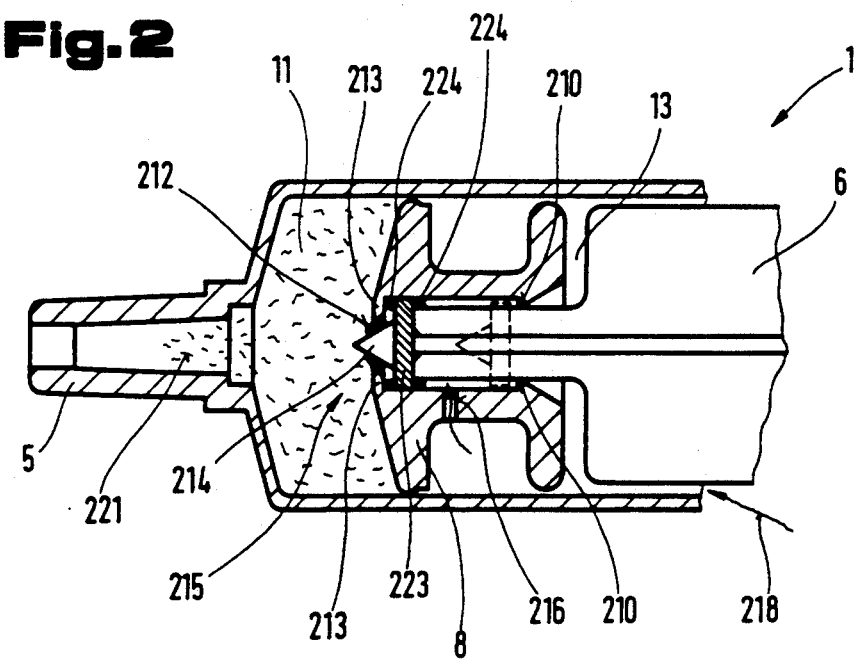
FIG. 2 is a fragmentary view of the syringe when the injection fluid taken up in it has been partly pressed out, showing a different embodiment of an inner piston.

FIG. 2 shows a syringe 1 substantially the same as in FIG. 1, the only difference being the form of the inner piston 223. In this embodiment, the inner piston 223 is sealed off from the piston 8 by peripheral sealing rings 224 at the front end of the inner piston. It will be seen from FIG. 2 that, as the piston rod 6 is pushed forwards, the inner piston 223 is moved forwards until it meets the stops 213. Before the piston 8 comes into contact with the stops 213, however, the tip of spike 214 severs the weakened section 212. After the forward movement of the inner piston 223 and its engagement with stops 213, the spike assumes the position shown in FIG. 2. In this position, an appropriately strong force can be applied through the piston rod 6 to push the whole piston 8 forwards towards the injection needle and the outlet 5 so that injection fluid 221 can be discharged from the cylindrical chamber 11.

If the syringe 1 were to be used a second time, it is first necessary to draw the inner piston 223 back from the FIG. 2 position into the FIG. 1 position. Since the inner piston 206 or 223 is in contact with the stops 210, the whole piston 8 can, therefore, be entrained in a movement in the direction of the arrow 222, to create an adequate partial vacuum in the chamber 11 so that injection fluid 221 can enter. However, this is not possible with the syringe 1 described: even if spike 215 has been drawn back into the broken line position shown in FIG. 2, the punctured sealing element remains open. The ambient air, indicated by arrow 218, thus enters the chamber 11 through the chamber 13 and the venting aperture 216 so that an adequate partial vacuum cannot be created in the chamber 11 to suck up injection fluid 221.

This is a sure way of preventing the syringe 1 according to the invention from being used several times. The filling of more injection fluid is reliably prevented by the safeguard against reuse, which is located in the piston and formed by the sealing element 211 with the weakened section 212 and the piercing spike 214.

Another embodiment of a syringe 1 according to the invention is shown in FIGS. 3 to 7. It is of substantially the same type of construction as the syringe 1 of FIG. 1, and identical reference numerals designate identical parts. It differs from the syringe 1 shown in FIGS. 1 and 2 only in the construction of the safeguard against reuse 201. In this embodiment, too, there is an inner piston 223 connected to the piston rod 6 in addition to the piston 8. The movement of the piston 223 is then limited in both directions by stops 210 or 213. The internal space 217 of the bore 205 containing the inner piston 223 is again connected by a venting aperture 216 to a chamber 13 in the cylinder 2, which is separated from the chamber 11 by the piston 8. In this case, the safeguard against reuse comprises a piercing spike 214 which acts as the opening member 215 and projects a distance 225 beyond an end 226 of the inner piston 223, as is also the case in FIGS. 1 and 2. In this case, though, the distance 225 is greater since spreading elements 227 are arranged between the spike 214 and the end 226.

The length 225 of the spike 214 and spreading elements 227 is in any event greater than a distance 228 between a contact surface 229 of the stop 213 for the inner piston 223 and the sealing membrane 230 which forms the sealing element 211 for the bore 205. It will be seen from FIG. 4 that the spreading elements 227 are formed by four lugs projecting at 90° from one another. FIG. 6 shows that the piston rod 6 has a cross-shaped cross section. As shown in this figure, a diameter 208 of a circle enveloping the piston rod 6 is smaller than the diameter of the inlet opening 209 (shown in broken lines in FIG. 6) in the region of a rear end 231 of the piston 8. The inlet opening 209 converges conically towards the outlet 5, thus facilitating insertion of the inner piston 223.

The syringe of FIGS. 3 to 7 operates as follows:

If the piston in the FIG. 3 position is entrained in the direction of the arrow 222 by movement of the inner piston 223, the injection fluid can be filled through the outlet 5. The relative positions of the inner piston 223 and the piston 8 during the filling of the injection fluid can be seen best from FIG. 5. An adequate partial vacuum can be created in the chamber 11 since the bore 205 is closed by the sealing membrane 230.

If the injection fluid is to be pressed out through the outlet 5, the inner piston 223 must be put into the FIG. 7 position relative to the piston 8. But this displacement of the inner piston 223 causes the spike 214 to puncture the sealing membrane 230. The membrane is then torn open by the following spreading elements 227 so that a sufficiently direct connection is established between the chamber 11 and the air space between the membrane 230 and the end 226 of the inner piston 223.

This is a simple way of preventing air bubbles from being carried along with the injection fluid when it is pressed out of the chamber 11 after the syringe 1 has been vented.

Reuse of the syringe 1 is made impossible in the same manner as described hereinabove. It is again possible to predefine a volume displacement by which the inner piston 223 can be displaced relative to the piston 8 without ambient air 218 entering the chamber 11 by selecting a suitable longitudinal spacing 232 or stroke of the inner piston 223 for so-called aspiration. This process is necessary to ascertain whether the needle has pierced a vein when it enters the animal or human body so that any injection fluids which have to be injected directly into the bloodstream can be checked for this immediately. With injection fluid which must not go into the bloodstream, on the other hand, it is possible to establish whether or not a vein has actually been pierced.

Syringe 1 must be handled sensitively since otherwise ambient air 218 may again enter the chamber 11 if the inner piston 223 overshoots the venting aperture 216. In this case, the injection process has to be interrupted to remove the air from the chamber 13.

FIGS. 8 to 10 show a different embodiment of a syringe 1, with different positions of the piston 8 and inner piston 223, identical reference numerals again designating identical parts. In this embodiment, the space 217 in the bore 205 and the piston 8 is shut off from the chamber 11 by a disc 233 forming the sealing element 211. The disc 233 is inserted in a recess 234 and snapped in. It may have retaining members 235 projecting beyond the stops 213 by a distance 236 greater than the depth 237 of the recess 234 receiving the disc 233. As will be explained later, the retaining members 235 can prevent the disc from dropping into the chamber 11 and possibly blocking the outlet 5 even when it is released.

It will further be seen from FIGS. 8 to 10 that the sealing effect between the piston 8 and the inner piston 223 and between the piston 8 and the cylinder 2 can be produced by piston rings 238 or by O-rings or other sealing elements. The arrangement of the sealing disc 233 makes it possible to carry out aspiration, so that when the syringe 1 has been positioned and the injection needle 4 inserted in the animal or human body, it is highly probable that no air can enter the chamber 11. As explained with reference to the preceding embodiments, injection fluid can be sucked up by moving the piston 8 back in the direction of the arrow 222 but in order to discharge the injection fluid 221 from the chamber 11, the inner piston 223 has to be placed in the FIG. 9 position. Since power cannot be transmitted from the piston rod 6 to the piston 8 until the inner piston 223 is in contact with the stops 213, the sealing disc 233 is punctured by the spike 214, as shown in FIGS. 9 and 10, before the piston 8 moves towards the outlet 5. By having the material rigid enough even int he weakened section 212 of the disc 233 and by having the disc 233 inserted firm enough in the recess 234, it is possible for the spike 214 to penetrate the disc 233 and impale it between itself and the spreading elements 227. Thus, the disc is pushed out of the recess 234 and raised, as shown in FIG. 9. This state is reached during the deaeration of the syringe, when a certain amount of injection fluid 221 has to be pressed out of the chamber 11. The chamber 11 can also be deaerated in this position. This is usually done by the doctor or nurse giving the injection; they knock on the syringe to bring the air bubbles to near the outlet 5, and then discharge injection fluid 221 until the air bubbles have passed through the needle.

When the syringe 1 has been deaerated, the injection needle 4 is inserted in the body, whereupon the inner piston 223 is drawn back relative to the piston 8 with the piston rod 6, until the disc 233 is in the FIG. 10 position. If the engagement between the spike 214 and the disc 233 is strong enough, the piston 8 can even be drawn back a short distance by means of the piston rod 6, before the spike 214 is removed from the disc 233. On the other hand, the distance between the spike 214 and the end 226 of the inner piston 223 facing towards it may be dimensioned so that the movement of the inner piston 223 causes enough injection fluid to be sucked up, for a person to see from the transparent part of the syringe 1, namely the cylinder 2, whether or not a vein has been pierced. This can be seen by whether or not blood is sucked into the chamber 11 when the piston rod 6 is drawn back. By moving the piston rod 6 in the opposite direction to the arrow 222, with the inner piston 223 adopting the FIG. 9 position relative to the piston 8, the requisite amount of injection fluid 221 can then be injected into the body from the chamber 11. Care must be taken to locate the venting aperture 216 so that, when the spike 214 is held in the disc 233 and the disc 233 is inserted in the recess 234, the inner piston 223 is still located between the aperture 216 and the stops 213. Otherwise, there would again be a danger of air entering the chamber 11 through the aperture 216. This construction of the syringe meets all the medical requirements and allows for aspiration and yet, if an attempt is made to suck up more injection fluid when it has been discharged, the energy which this requires will make the inner piston 223 come out of the disc 233 and move into the FIG. 8 position. But with the disc 233 broken, no vacuum will be created in the chamber 11 through the venting aperture 216 when the piston rod 6 is pulled further back, and no more injection fluid 221 can be sucked up.

It is possible to provide a plurality of spikes 214, for example on individual fins or spreading elements 227, or slimmer tips or knife-edge members or the like may be used. It is important for the weakened sections 212 to be severed without exerting too much force so that the amount of force required to press injection fluid 221 out of the chamber 11 will dependably break the sealing element 211, thereby preventing any reuse of the syringe.

Figure 11:
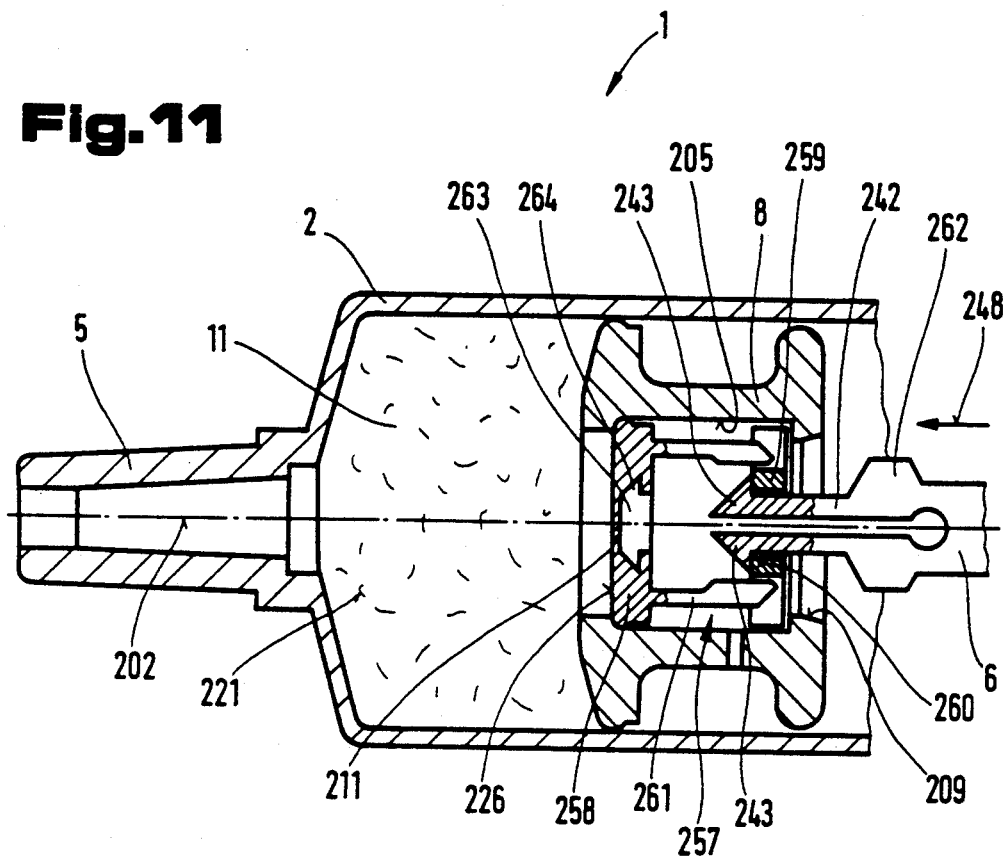
FIG. 11 is a cross sectional side view of a different embodiment of a syringe according to the invention, with a two-part inner piston, in the position where the injection fluid is being drawn up into the interior.
Figure 12:
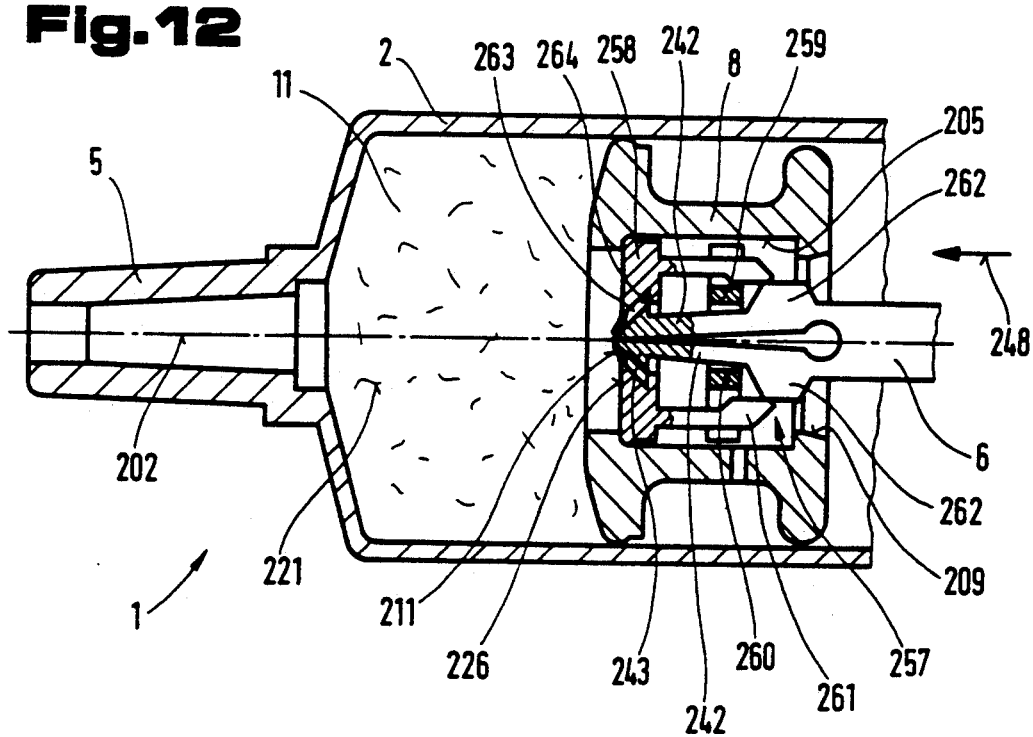
FIG. 12 is a cross sectional side view of the syringe of FIG. 11, in a greatly simplified diagrammatic representation, in the position where the injection fluid is being pressed out of the interior and a further attempt is being made to draw up another injection fluid.

FIGS. 11 and 12 show an arrangement where the inner piston 257 arranged in the piston 8 comprises two parts 258 and 259. The part 258 is disc-like and is applied to the bore 205 in the piston 8 with a sealing action. The part 259 comprises a cross-or plus-shaped plate containing an opening 260. Locking arms 242, which are integral with the piston rod 6 and linked with it for movement, extend through the opening 260. The arms 242 have arresting lugs 243, which are directed radially outwardly and which engage below the part 259 from the side facing towards the part 258. The part 258 further has control arms 261 of substantially the same length as the bore 205. The beam-like arms of the part 259 of the inner piston 257 acting as a supporting plate are each arranged between two such control arms 261. Control members 262 are arranged on the locking arms 242 at a spacing smaller than the length of the bore 205. The control members 262 have an enveloping circle diameter substantially corresponding to the diameter of the inlet opening 209 leading into the bore 205.

The part 258 is designed to seal a surface in the region of a front and 226. At the side facing towards the part 259, it contains a recess 263 with undercut portions 264, designed to receive the arresting lugs 243 of the arms 242. The syringe 1 prepared for use is supplied with the part 259 lying loosely in the part 258 of the inner piston 257, and with the lugs 243 of the locking arms only engaging behind the part 259. If an appropriate amount of injection fluid 221 is to be drawn up by the syringe, the piston rod 6 is pulled back in the opposite direction to the arrow 248. The part 259 thereby entrains the piston 8 and a vacuum is accordingly created in the chamber 11, causing the injection fluid to be sucked in.

Once an appropriate amount of injection fluid is contained in the syringe 1, pressure can be exerted on the piston 8 by the part 258, causing injection fluid to be discharged through the outlet 5, by pushing the piston rod 6 forwards in the direction of the arrow 248. The pressure thus exerted causes the arms 242 to enter the recess 263, and their lugs 243 to catch in the undercut portion 264. If the piston rod 6 is drawn back again in the opposite direction to the arrow 248, e.g. for aspiration, the part 258 with the control arms 261 will also move in the direction of the inlet opening 209. The arms 261 are squeezed in the opening 209. On further movement of the piston rod 6 in the opposite direction to the arrow 248, the control members 262 move onto the control arms 261, causing the locking arms 242 to be pressed radially inwardly int he direction of the longitudinal axis 202. The arms 242, therefore, come out of the undercut portions 264, and the arresting lugs 243 have an enveloping circle diameter smaller than the diameter of the opening 260 in the part 259 of the inner piston 257. If a force is exerted on the piston rod 6 in the opposite direction to the arrow 248, the piston rod 6 will be drawn out loosely without any further movement of the piston 8. Thus, it can be drawn back for aspiration until slightly stronger resistance is met, i.e. when the control members 262 move onto the control arms 261. The space required for aspiration is provided by drawing back the inner piston 257 in the bore 205. But even if the piston rod 6 is drawn back too vigorously and comes out of the piston 8 during aspiration, it is possible to push it back into the piston 8 in the direction of the arrow 248, although recoupling is prevented. Even if the piston rod 6 happens to be inserted so that it again locks into the parts 258 and 259, it will certainly be uncoupled by the interaction of the control members 262 and control arms 261 when it is moved back in the opposite direction to the arrow 248. With this embodiment of the syringe, aspiration is possible but deliberate use of the syringe for the second time is avoided.

I claim:

1. An injection syringe comprising
   (a) a cylinder having a longitudinal axis extending between opposite ends of the cylinder,
   (b) a piston guided in the cylinder and dividing the cylinder into two cylinder chambers respectively facing the opposite cylinder ends,
   (c) a piston rod coupled to the piston and extending in one of the cylinder chambers and through one cylinder end,
   (d) a coupling arrangement at a cylinder end opposite to the one end for coupling an injection needle held by the coupling arrangement to the cylinder, the piston and the opposite cylinder end defining the other cylinder chamber, and
   (e) a safeguard against reuse of the injection syringe, the safeguard comprising
      (1) an inner piston connected to the piston rod for movement therewith and guided in a bore in the piston, the bore extending parallel to the longitudinal cylinder axis,
      (2) respective stops delimiting the piston bore towards the other cylinder chamber and the piston rod whereby the inner piston is coupled to the piston, the stops projecting inwardly into the path of the movement of the inner piston in the bore for engagement with the inner piston,
      (3) a frangible sealing element at an end of the bore remote from the piston rod for sealing the bore from the other cylinder chamber,
      (4) a piercing spike projecting from an end of the inner piston facing the sealing element for opening the frangible sealing element upon movement of the inner piston towards the remote bore end, and
      (5) a venting aperture in the piston spaced from the remote bore end and connecting the piston bore with the ambient atmosphere, the venting aperture being positioned between the inner piston and the sealing element when the inner piston engages the stops delimiting the piston bore towards the piston rod.

2. The injection syringe of claim 1, wherein the piston rod, the piston, the inner piston, the piercing spike and the sealing element are arranged coaxially along the longitudinal cylinder axis.

3. The injection syringe of claim 1, wherein the piston comprises a guiding projection at an end of the piston facing the piston rod for guiding the piston in the cylinder.

4. The injection syringe of claim 1, further comprising spreading elements projecting from the end of the inner piston and arranged radially adjacent the piercing spike.

5. The injection syringe of claim 1, further comprising piston rings respectively arranged between the piston and the cylinder, and the inner piston and the piston bore.

6. The injection syringe of claim 1, further comprising retaining members mounting the sealing element in an opening in the opposite cylinder end, the retaining members engaging the stops delimiting the piston bore towards the other cylinder chamber, and a distance between the sealing element and the stops being greater than the depth of the opening.

7. The injection syringe of claim 1, wherein the piercing spike has a length extending from the end of the inner piston which is greater than the distance between the sealing element and abutment faces of the stops engaged by the inner piston.

* * * * *